United States Patent [19]

Hubele et al.

[11] 4,076,836

[45] Feb. 28, 1978

[54] ACYLATED PHENYLAMINE THIOPROPIONATES USEFUL IN COMBATTING PLANT FUNGI

[75] Inventors: Adolf Hubele, Magden; Walter Kunz, Oberwil, both of Switzerland; Wolfgang Eckhardt, Lorrach, Germany

[73] Assignee: Ciba-Geigy Corporation, Ardsley, N.Y.

[21] Appl. No.: 726,348

[22] Filed: Sep. 24, 1976

[30] Foreign Application Priority Data

Sep. 30, 1975 Switzerland .................... 12648/75

[51] Int. Cl.$^2$ ............................................. A61K 31/34
[52] U.S. Cl. .................................. 424/285; 424/251; 424/275; 424/248.52; 260/256.5 R; 260/293.73; 260/294.8 R; 260/327 P; 260/329 S; 544/159

[58] Field of Search ..................... 260/347.2; 424/285

[56] References Cited

U.S. PATENT DOCUMENTS 3,766,244  10/1973  Giacobbe et al. ............... 260/471 A
3,830,829  8/1974  Olin ................................ 260/473 G

OTHER PUBLICATIONS

Hubele, Chem. Abstracts, vol. 84, (1976) 17120w.

*Primary Examiner*—Henry R. Jiles
*Assistant Examiner*—Bernard Dentz
*Attorney, Agent, or Firm*—Harry Falber

[57] ABSTRACT

Acylated phenylamino thiopropionates of the formula I shown hereinafter are effective microbicides. They may be used for combatting plantpathogenic fungi or for preventing plants from fungi attack.

11 Claims, No Drawings

ACYLATED PHENYLAMINE THIOPROPIONATES USEFUL IN COMBATTING PLANT FUNGI

The present invention provides compounds of the formula I

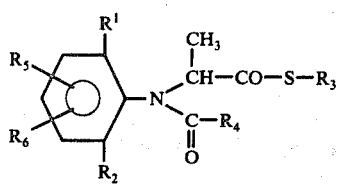

wherein
$R_1$ represents a $C_1$-$C_4$-alkyl or $C_1$-$C_4$-alkoxy group or a halogen atom,
$R_2$ represents a $C_1$-$C_3$-alkyl or $C_1$-$C_4$-alkoxy group or a halogen atom,
$R_5$ represents a hydrogen atom, a $C_1$-$C_3$-alkyl group or a halogen atom,
$R_6$ represents a hydrogen atom or a methyl group, with the proviso that the total number of carbon atoms contained by the substituents $R_1$, $R_2$, $R_5$ and $R_6$ in the phenyl ring does not exceed 8,
$R_3$ represents a methyl or ethyl group, and
$R_4$ represents a 5- or 6-membered heterocyclic ring which is unsubstituted or substituted by methyl and/or halogen and which contains 1 or 2 heteroatoms, a process for the manufacture thereof, compositions which contain these compounds as active components, and a method of using these active components as microbicides.

By alkyl and alkyl moiety of an alkoxy group are meant the following groups, depending on the stated number of carbon atoms: methyl, ethyl, n-propyl, isopropyl, or n-butyl, iso-butyl, sec. or tert. butyl. By halogen is meant fluorine, chlorine, bromine or iodine.

As a 5- to 6-membered heterocyclic ring there may be cited by way of example: furane, thiophene, pyridine, pyrimidine, 2,3-dihydro-4H-pyrane, 1,4-oxathi-(2)-ine, tetrahydrofurane, morpholine or piperidine, which can be unsubstituted or substituted by methyl and/or halogen.

The compounds (2'-methylfuranyl-3'-)carbonyl-2,6-dimethylaniline and (2'-methylfuranyl-3'-)-carbonyl-2-methyl-6-chloroaniline are known from DOS No. 2,006,471 as active substances having moderate action on certain fungi (Uromyces phaseoli, Alternaria solani, Rhizoctonia solani).

The present invention is based on the surprising observation that compounds having the markedly differing structure of the formula I possess for practical purposes a very advantageous microbicidal spectrum for protecting cultivated plants. Examples of cultivated plants within the scope of this invention are: cereals, maize, rice, vegetables, sugar-beet, soya, ground nuts, fruit trees, ornamentals, but primarily vines, hops, cucumber plants (cucumber, marrows, melons), solanaceae, such as potatoes, tobacco plants and tomatoes, and also banana, cocoa and natural rubber plants.

With the active ingredients of the formula I it is possible to inhibit or destroy the fungi which occur in plants or parts of plants (fruit, blossoms, leaves, stems, tubers, roots) in these and also related crops of useful plants, and also to protect from such fungi the parts of plants which grow later. The active ingredients are effective against the phytopathogenic fungi which belong to the following classes: Ascomycetes (e.g. Erysiphaceae); Basidiomycetes, chiefly rust fungi; fungi imperfecti, such as chiefly the genus Fusarium; but especially against the Oomycetes belonging to the class of the Phycomycetes, such as Phytophthora, Peronospora, Pseudoperonospora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

Preferred microbicides are compounds of the formula I in which $R_1$ represents a methyl or ethyl group or a chlorine atom, whilst $R_3$, $R_4$, $R_5$ have the meanings already assigned to them. These compounds shall be referred to as group Ia.

A group of microbicidally interesting compounds belonging to group Ia to be singled out for special mention comprises those compounds wherein $R_4$ represents the 2-tetrahydrofuranyl group. These compounds shall be referred to as group Ib.

Compounds belonging to the group Ia which are also to be singled out for special mention are those wherein $R_4$ represents the 2-furanyl group. These compounds shall be referred to as group Ic.

Within these two last mentioned groups, compounds which are of particular importance as microbicides are those wherein $R_3$ represents the methyl group and wherein the total number of carbon atoms contained by the substituents $R_1$, $R_2$, $R_5$ and $R_6$ does not exceed 4, for example the 2,3,5,6-tetramethylaniline, 2,6-dimethyl-3-ethylaniline, 2,4,6-trimethylaniline, and 2,6-dimethylaniline derivatives, and also further 2,6-dimethylaniline derivatives which contain in the phenyl nucleus another substituent $R_5$ or $R_6$ which is different from hydrogen. Such compounds of both groups Ib and Ic shall be referred to as group Id.

The compounds of the formula I are obtained by initially reacting for example a compound of the formula II

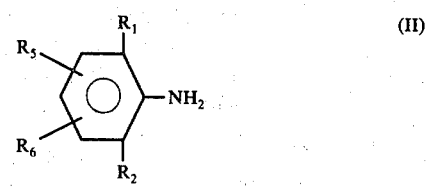

wherein $R_1$, $R_2$, $R_5$ and $R_6$ are as defined in formula I, with a compound of the formula III

(in which X and $R_3$ are as defined in formula I and Hal represents a halogen atom, preferably a chlorine or bromine atom), and then, according to the invention, reacting the compound of the formula IV

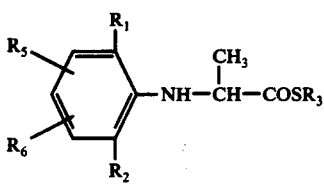

(IV)

obtained in this or another manner, with a carboxylic acid of the formula V

HO—COR$_4$  (V)

or with the reactive acid halide, acid anhydride, ester or amide thereof, preferably with the halide or anhydride.

In the above mentioned formulae IV and V, the symbols R$_1$ to R$_6$ have the meanings assigned to them in the formula I. Preferred acid halides are the acid chlorides or acid bromides.

The reactions can be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ethers and ethereal compounds, such as dialkyl ethers, dioxane, tetrahydrofurane; nitriles, such as acetonitrile; N,N-dialkylated amides, such as dimethyl formamide; dimethyl sulphoxide; ketones, such as methyl ethyl ketone, and mixtures of such solvents.

The reaction temperatures are between 0° and 180° C, preferably between 20° and 120° C. It is often advantageous to use acid acceptors or condensation agents. Suitable examples are: tertiary amines, such as trialkylamines (for example triethylamine), pyridine and pyridine bases, or inorganic bases, for example the oxides and hydroxides, hydrogen carbonates and carbonates of alkali metals and alkaline earth metals, and sodium acetate. Moreover, in the process for obtaining the intermediate of the formula IV, it is possible to use an excess of the respective aniline derivative of the formula II as acid acceptor.

The process in which compounds of the formula II are used as starting materials can also be carried out without acid acceptors. On some occasions it is expedient to introduce nitrogen in order to expel the hydrogen halide that has formed, and on others it is very advantageous to use dimethyl formamide as reaction catalyst.

Particulars on the manufacture of the intermediates of the formula IV can be inferred from those methods which are generally indicated for the manufacture of anilinoalkanoic acid esters in the following publications:

J.Org. Chem. 30, 4101 (1965); Tetrahedron 1967, 487; Tetrahedron 1967, 493.

The compounds of the formula I contain an asymmetrical carbon atom in the thiopropionate side-chain and can be resolved into the optical antipodes in the customary manner. In this connection, the enantiomeric D-form has the more pronounced microbicidal action.

Within the scope of the invention, those compounds, the compositions which contain them and their use, which refer to the D-configurations of the formula I, are accordingly preferred. These D-forms usually have in ethanol or acetone a negative angle of rotation.

The pure optical D-antipodes are obtained by manufacturing for example the racemic compound of the formula VI

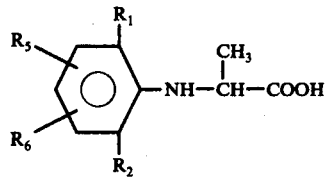

(VI)

wherein R$_1$, R$_2$, R$_5$ and R$_6$ are as defined in formula I, obtained from reacting the aniline of the formula II with α-halogenopropionic acid, then reacting it in known manner with a nitrogen-containing optically active base to give the corresponding salt. The pure D-form is obtained stepwise by fractional crystallisation of the salt and subsequent liberation of the acid of the formula VI which is enriched with the optical D-antipode and, if appropriate, repetition (also several times) of the salt formation, crystallisation and liberation of the α-anilino-propionic acid of the formula VI. From this pure D-form it is then possible, if desired, to obtain the optically active ester of the formula IV in known manner, for example with methyl mercaptan or ethyl mercaptan, or preferably with their salts, in particular their sodium or potassium salts, and with the acid halide of the optical antipode of the formula VI. This ester is then reacted according to the invention with the corresponding compound of the formula V.

A suitable optically active organic base is for example α-phenylethylamine.

Irrespective of the cited optical isomerism, an atropisomerism is observed about the phenyl —N = axis in those instances in which the phenyl ring is substituted unsymmetrically to this axis (i.e. optionally also on account of the presence of additional substituents).

Provided no synthesis with the object of isolating pure isomers is carried out, a produce will normally occur as a mixture of two optical isomers or two atropisomers, or as a mixture of these four possible isomers. However, the basically more advantageous fungicidal action of the enantiomeric D-form (in comparison with the D,L-form or with the L-form) is retained and is not noticeably affected by the atropisomerism.

The following Examples will serve to illustrate the invention in more detail but do not limit it to what is described therein. Unless stated to the contrary, an active substance of the formula I which can occur in optically active forms is always to be understood as meaning the racemic mixture.

EXAMPLE 1

Manufacture of

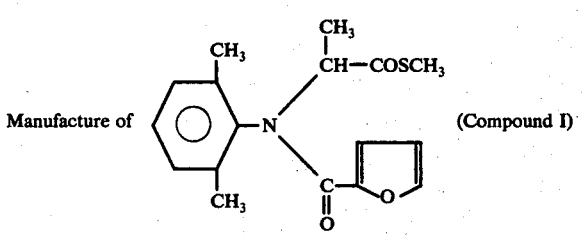

(Compound I)

N-(1'-Methylthiocarbonyl-ethyl)-N-(furane-(2")-carbonyl)-2,6-dimethylaniline.

a. Preparation of the Intermediate

A mixture of 24.2 g of 2,6-dimethylaniline, 95.3 g of thiomethyl 2-bromopropionate and 40.2 g of sodium bicarbonate was stirred for 10 hours at 120° C, then cooled, diluted with 100 ml of water and extracted with diethyl ether. The extract was washed with a small amount of water, dried over sodium sulphate, filtered, and freed from ether by evaporation. Excess thiomethyl 2-bromopropionate was distilled off and the crude product was then distilled in a high vacuum; b.p. 125°–127° C/0.1 Torr.

b. 13 g of furane-2-carboxylic chloride were slowly added dropwise to 19.2 g of the thiomethyl ester obtained in a) in 200 ml of absolute toluene. After the weakly exothermic reaction had subsided, stirring was continued for 12 hours. The reaction mixture was thereafter refluxed for 2 hours, cooled, washed with a small quantity of a saturated solution of sodium carbonate, dried over sodium sulphate, and filtered. After evaporation of the solvent, the residual oil was crystallised by trituraton with a small amount of petroleum ether. After recrystallisation from petroleum ether, the slightly beige coloured crystals of compound 1 melted at 111°–112° C.

The other intermediates, including for example the following compounds of the formula

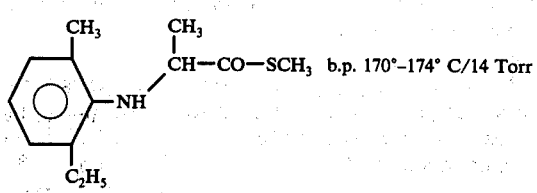

are also obtained in a manner analogous to that described in Example Ia).

The following compounds of the formula

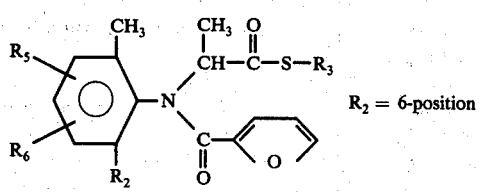

were obtained in this manner or by one of the methods described above.

| Compound | $R_2$ | $R_5$ | $R_6$ | $R_3$ | Physical constant (temperatures in ° C) |
|---|---|---|---|---|---|
| 1 | $CH_3$ | H | H | $CH_3$ | m.p. 111–112° |
| 2 | $C_2H_5$ | H | H | $CH_3$ | b.p. 169–171°/0.03 Torr |
| 3 | $CH_3$ | 4-$CH_3$ | H | $CH_3$ | m.p. 121–122° |
| 4 | $CH_3$ | 3-$CH_3$ | H | $CH_3$ | b.p. 175–180°/0.08 Torr |
| 5 | $CH_3$ | 3-$CH_3$ | 5-$CH_3$ | $CH_3$ | m.p. 122–126° |
| 6 | $CH_3$ | 4-Cl | H | $CH_3$ | m.p. 117–119° |
| 7 | Br | 4-Cl | H | $CH_3$ | m.p. 147–149° |
| 8 | $CH_3$ | H | H | $C_2H_5$ | b.p. 172–177°/0.03 Torr |
| 9 | $C_2H_5$ | H | H | $C_2H_5$ | b.p. 172–175°/0.03 Torr |
| 10 | $CH_3$ | 3-$CH_3$ | H | $C_2H_5$ | b.p. 176–180°/0.08 Torr |
| 11 | $CH_3$ | 3-$CH_3$ | 5-$CH_3$ | $C_2H_5$ | m.p. 125–128° |
| 12 | $C_2H_5$ | 3-$CH_3$ | H | $CH_3$ | m.p. 126–130° |
| 13 | $CH_3$ | 3-Br | H | $CH_3$ | m.p. 115–121° |

The following compounds of the formula

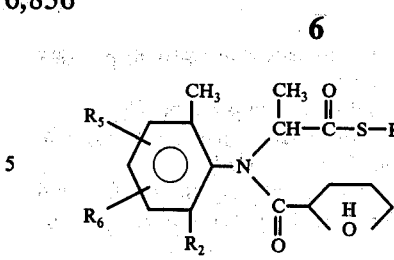

were obtained in this manner or by one of the methods described above.

| Compound | $R_2$ | $R_5$ | $R_6$ | $R_3$ | Physical constant (temperatures in ° C) |
|---|---|---|---|---|---|
| 14 | $CH_3$ | H | H | $CH_3$ | b.p. 180–184°/0.7 Torr |
| 15 | $C_2H_5$ | H | H | $CH_3$ | b.p. 153°/0.1 Torr |
| 16 | $CH_3$ | 4-$CH_3$ | H | $CH_3$ | b.p. 181–185°/0.7 Torr |
| 17 | $CH_3$ | 3-$CH_3$ | H | $CH_3$ | b.p. 182–185°/0.7 Torr |
| 18 | $CH_3$ | 3-$CH_3$ | 5-$CH_3$ | $CH_3$ | b.p. 199°/1 Torr |
| 19 | $CH_3$ | 4-Cl | H | $CH_3$ | b.p. 178–182°/0.6 Torr |
| 20 | $CH_3$ | H | H | $C_2H_5$ | b.p. 153.157°/0.08 Torr |
| 21 | $CH_3$ | 3-$C_2H_5$ | H | $CH_3$ | oil |
| 22 | $CH_3$ | 3-Br | H | $CH_3$ | viscous |
| 23 | Cl | H | H | $CH_3$ | b.p. 169–173°/0.08 Torr |

The following compounds were also obtained, in which especially the enantiomeric D-forms exhibit a pronounced microbicidal action:

Compound:

24) N-(1'-methylthiocarbonyl-ethyl)-N-(thiene-2"-carbonyl)-2,6-dimethylaniline, m.p. 133° C;

25) N-(1'-methylthiocarbonyl-ethyl)-N-(5"-bromofurane-2"-carbonyl)-2,6-dimethylaniline, m.p. 110°–118° C;

26) N-(1'-methylthiocarbonyl-ethyl)-N-(5"-bromofurane-2"-carbonyl)-2,4,6-trimethylaniline, m.p. 123°–124° C;

27) N-(1'-methylthiocarbonyl-ethyl)-N-(5"-bromofurane-2"-carbonyl)-2,3,6-trimethylaniline, b.p. 184°–189° C/0.02 Torr;

28) N-(1'-methylthiocarbonyl-ethyl)-N-(2",4"-dichloro-1",3"-pyrimidine-5"-carbonyl)-2,6-dimethylaniline, m.p. 152°–155° C.

The compounds of the formula I can be used by themselves or together with suitable carriers and/or other additives. Suitable carriers can be solid or liquid and correspond to the customary substances used in the art of formulation, for example natural or regenerated mineral substances, solvents, dispersants, wetting agents, tackifiers, thickeners, binders or fertilisers.

Compositions for commercial use contain from 0.1 to 90% of active substance.

For application, the compounds of the formula I may take and be used in the following forms (the percentages by weight indicated in brackets indicate advantageous amounts of active substance):

Solid forms: dusts and tracking agents (up to 10%); granulates, coated granulates, impregnated granulates and homogeneous granulates (1 to 80%);

Liquid forms:

a. active substance concentrates which are dispersible in water: wettable powders and pastes (25 to 90% in commercial package form, 0.01 to 15% in ready for use solution); emulsion concentrates and concentrated solutions (10 to 50%; 0.01 to 15% in ready for use solution).

b. Solutions (0.1 to 20%).

The active substances of the formula I of the present invention can be formulated for example as follows:

Dusts: The following substances are used to prepare a) a 5% and b) a 2% dust:
a. 5 parts of active substance 95 parts of talc;
b. 2 parts of active substance, 1 part of highly dispersed silicic acid, 97 parts of talc.

The active substances are mixed with the carriers and ground and in this form can be processed to dusts for application.

Granulate: The following substances are used to prepare a 5% granulate:
5 parts of active substance
0.25 parts of epichlorohydrin
0.25 parts of cetyl polyglycol ether
3.50 parts of polyethylene glycol
91 parts of kaolin (particle size 0.3 - 0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is particularly suitable for soil application.

Wettable powders: The following constituents are used to prepare a) a 70%, b) a 40%, c) and d) a 25% and e) a 10% wettable powder:

a.
70 parts of active substance
5 parts of sodium dibutyl naphthylsulphonate
3 parts of naphthalenesulphonic acid/phenolsulphonic acid/formaldehyde condensate (3:2:1)
10 parts of kaolin
12 parts of Champagne chalk b.
40 parts of active substance
5 parts of sodium lignin sulphonate
1 part of sodium dibutylnaphthalenesulphonic acid
54 parts of silicic acid c.
25 parts of active substance
4.5 parts of calcium lignin sulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin d.
25 parts of active substance
2.5 parts of isooctylphenoxy-polyoxyethylene-ethanol
1.7 parts of a Champagne chalk/hydroxyethyl cellulose mixture (1:1)
8.3 parts of sodium aluminium silicate
16.5 parts of kieselguhr
46 parts of kaolin e.
10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

Emulsifiable concentrates: The following substances are used to prepare a 25% emulsifiable concentrate:
25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting this concentrate with water it is possible to prepare emulsions of the desired concentration, which are especially suitable for leaf application. The compounds of the formula I can be used with other suitable pesticides or active substances which promote plant growth in order to broaden their activity spectrum.

EXAMPLE 2

Action on Phytophthora infestans on tomato plants

I. Residual preventive action

Tomato plants of the "Roter Gnom" variety are infected when 3 weeks old with a zoospore suspension of Phytophthora infestans after they have been sprayed with a broth (prepared from the active substance formulated as a wettable powder) containing 0.05% of active substance, and dried. The plants are then kept for 6 days in a climatic chamber at 18° to 20° C and high humidity, which is produced by means of an artificial wet fog. After this time typical leaf specks appear. The effectiveness of the tested substance is assessed by determining the number and size of these specks.

Ib. Curative Action

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the plants have dried, they are sprayed with a broth which contains the active substance formulated as a wettable powder in a concentration of 0.05%. After the spray coating has dried, the plants are again kept in the humid chamber for 4 days. The effectiveness of the tested substances is assessed by determining the size and number of the typical leaf specks which have occurred during this time.

II. Preventive-systemic action

The active substance is applied as a wettable powder in a concentration of 0.05% (referred to the volume of the soil) to the surface of the soil of 3 week old "Roter Gnom" tomatoes in pots. Three days later the underside of the leaves of the plants are sprayed with a zoospore suspension of Phytophthora infestans. The plants are then kept in a spray chamber at 18° to 20° C and saturated humidity for 5 days, after which time typical leaf specks form. The effectiveness of the tested substance is assessed by determining the size and number of the specks.

In these three tests, the compounds of the formula I, and especially those of group Ia, effect a pronounced leaf-fungicidal action compared with untreated, infected control plants (100% attack). Above all, compounds of the group Id, for example compounds 1, 4, 5, 6, 13, 14, 15, 17, 18, 21 and 22, prevent attack completely or almost completely (0 to 5% fungus attack) even when applied at an active substance concentration of 0.02%. The closest comparable compound known from DOS 2,006,471, N-(2'-methylfuranyl-3'-carbonyl)-2,6-dimethylaniline, inhibits the fungus attack to only 20 to 40% at an active substance concentration of 0.05% and to 50 to 100% (=no action) at a concentration of 0.02%. At the same time, a degree of phytotoxicity is observed.

EXAMPLE 3

Action on plasmopara viticola (Bert. et Curt.) (Bert. et de Toni) on vines a. Residual preventive action Vine cuttings of the variety "Chasselas" were reared in a greenhouse. Three plants in the 10 leaf stage were sprayed with a broth (containing 0.05% of active substance) prepared from the active substance and formulated as a wettable powder. After the coating layer had dried, the plants were infected on the underside of the leaves with the spore suspension of the fungus. The plants were subsequently kept in a humic chamber for 8 days, after which time symptoms of the disease were visible on the control plants. The effectiveness of the tested substances was assessed by determining the number and size of the infected areas in the treated plants.

b. Curative action

Vine cuttings of the variety "Chasselas" were reared in a greenhouse and infected in the 10 leaf stage on the underside of the leaves with a spore suspension of Plasmopara viticola. After they had been kept for 24 hours in a humid chamber, the plants were sprayed with a 0.05% broth prepared from a wettable powder of the active substance.

The plants were then kept in a humid chamber for a further 7 days, after which time the symptoms of the desease were visible on the control plants. The effectiveness of the tested substances was assessed by determining the size and number of the infected areas.

Compared with untreated, infected control plants (=100% fungus attack), the compounds of the formula I, and especially those of groups Ib and Ic, exhibit a predominantly good leaf-fungicidal action in both these tests. Above all, compounds of group Id, for example compounds 1 to 5, 13 to 19 and 21 to 23, prevent attack completely or almost completely (0 to 5%) even when applied at an active substance concentration of 0.02%. Compound 1 has a particularly lasting effect.

We claim:

1. A compound of the formula I

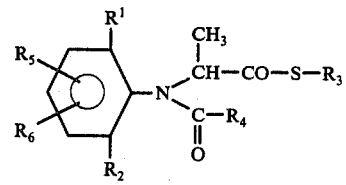

wherein
$R_1$ represents a $C_1$–$C_4$-alkyl or $C_1$–$C_4$-alkoxy group or a halogen atom,
$R_2$ represents a $C_1$–$C_3$-alkyl or $C_1$–$C_4$-alkoxy group or a halogen atom,
$R_5$ represents a hydrogen atom, a $C_1$–$C_3$-group or a halogen atom,
$R_6$ represents a hydrogen atom or a methyl group, with the proviso that the total number of carbon atoms contained by the substituents $R_1$, $R_2$, $R_5$ and $R_6$ in the phenyl ring does not exceed 8,
$R_3$ represents a methyl or ethyl group, and
$R_4$ represents 2-furanyl or 2-tetrahydrofuranyl unsubstituted or substituted by methyl or halogen.

2. A compound of the formula I according to claim 1, wherein $R_1$ represents a methyl group and $R_2$ represents a methyl or ethyl group or a chlorine atom.

3. A compound of the formula I according to claim 2, wherein $R_4$ represents the 2-tetrahydrofuranyl group.

4. A compound of the formula I according to claim 2, wherein $R_4$ represents the 2-furanyl group.

5. A compound of the formula I according to claim 3, wherein $R_3$ represents the methyl group and the total number of carbon atoms contained by the substituents $R_1$, $R_2$, $R_5$ $R_6$ does not exceed 4.

6. N-(1'-Methylthiocarbonyl-ethyl)-N-(furane-2"-carbonyl)-2,6-dimethylaniline according to claim 1.

7. N-(1'-Methylthiocarbonyl-ethyl)-N-(tetrahydrofurane-2"-carbonyl)-2,6-dimethylaniline according to claim 1.

8. A compound of the formula I according to claim 4 wherein $R_3$ represents the methyl group and the total number of carbon atoms contained by the substituents $R_1$, $R_2$, $R_5$ and $R_6$ does not exceed 4.

9. A phytopathogenic fungicidal composition which contains as active ingredient a fungicidally effective amount of a compound as claimed in claim 1, together with a suitable inert carrier therefor.

10. A method of controlling phytopathogenic fungi or of preventing attack by fungus, which comprises applying to plants, parts of plants or their environment, a fungicidally effective amount of a compound of the formula I as claimed in claim 1.

11. A method of protecting seeds, fruit, tubers and grains from fungus attack, which comprises applying to the above or their environment, a fungicidally effective amount of a compound of the formula I as claimed in claim 1.

* * * * *